United States Patent
Ikebukuro et al.

(10) Patent No.: US 8,721,853 B2
(45) Date of Patent: May 13, 2014

(54) FRUCTOSYL PEPTIDYL OXIDASE

(75) Inventors: Kazunori Ikebukuro, Fuchu (JP); Koji Sode, Fuchu (JP)

(73) Assignees: Roche Diagnostics Operations, Inc., Indianapolis, IN (US); Ultizyme International, Ltd, Tokyo (JP)

( * ) Notice: Subject to any disclaimer, the term of this patent is extended or adjusted under 35 U.S.C. 154(b) by 0 days.

(21) Appl. No.: 13/365,384

(22) Filed: Feb. 3, 2012

(65) Prior Publication Data

US 2012/0202235 A1    Aug. 9, 2012

Related U.S. Application Data (63) Continuation of application No. PCT/EP2010/004707, filed on Aug. 2, 2010.

(30) Foreign Application Priority Data

Aug. 3, 2009  (EP) .................................... 09009968

(51) Int. Cl.

| | | |
|---|---|---|
| *C12Q 1/00* | (2006.01) | |
| *C12Q 1/37* | (2006.01) | |
| *C12N 9/00* | (2006.01) | |
| *C12N 9/06* | (2006.01) | |
| *C07H 21/04* | (2006.01) | |

(52) U.S. Cl.
USPC ........ 204/403.14; 435/23; 435/183; 435/191; 536/23.2

(58) Field of Classification Search
None
See application file for complete search history.

(56) References Cited

U.S. PATENT DOCUMENTS

| 5,286,362 | A | 2/1994 | Hoenes et al. |
| 5,334,508 | A | 8/1994 | Hoenes |
| 5,997,817 | A | 12/1999 | Crismore et al. |
| 6,036,919 | A | 3/2000 | Thym et al. |
| 7,008,799 | B1 | 3/2006 | Zimmer et al. |
| 7,588,910 | B2 | 9/2009 | Matsuoka et al. |

FOREIGN PATENT DOCUMENTS

| CN | 1823166 A | 8/2006 |
| EP | 1 291 416 | 3/2003 |
| EP | 2 020 439 | 2/2009 |
| EP | 1 593 339 A1 | 9/2010 |
| EP | 1 626 088 | 12/2010 |
| EP | 2354224 | 8/2011 |
| JP | 11 046769 | 2/1999 |
| JP | 2010-104278 | 5/2010 |
| JP | 2010-115189 | 5/2010 |
| WO | WO 2004/113900 | 12/2004 |
| WO | WO 2007/094354 | 8/2007 |
| WO | WO 2007/125779 | 11/2007 |
| WO | WO 2007/128542 | 1/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Ferri et al. J Diabetes Sci Technol. May 1, 2009;3(3):585-92.*
Accession Q0UIL6. Sep. 5, 2006.*
Campas et al.; "Enzyme inhibition-based biosensor for the electrochemical detection of microcystins in natural blooms of cyanobacteria"; Science Direct; Elsevier, Talanta 72 (2007), pp. 179-186.
Hirokawa et al.; "Molecular cloning and expression of novel fructosyl peptide oxidases and their application for the measurement of glycated protein"; Elsevier, Biochemical and Biphysical Research Communicatios, 331 (2003), pp. 104-111, XP 004465110, ISSN 0006-291X.
Maguire; "Elimination of the "Chromogen Oxidase" Activity of Bilirubin Oxidase Added to Obviate Bilirubin Interference in Hydrogen Peroxide/Peroxidase Detecting Systems"; Clinical Chemistry, vol. 31, No. 12, pp. 2007-2008 (1984); OX 002603204.
Yoshida; "Primary structures of fungal fructosyl amino acid oxidases and their application to the measurement of glycated proteins"; European Journal of Biochem, vol. 242, No. 3, 1996, pp. 499-505, OX002561949, ISSN 0014-2956.
International Search Report; PCT/EP2010/004707.

* cited by examiner

*Primary Examiner* — Christian Fronda
(74) *Attorney, Agent, or Firm* — Krieg DeVault LLP (57) ABSTRACT

In one form, a fructosyl peptidyl oxidase derived from a budding yeast *Phaeosphaeria nodorum* for assaying a glycated protein in a sample is provided. The fructosyl peptidyl oxidase has higher activity toward fructosyl valine as well as fructosyl valyl histidine, and may be useful in assaying HbA1c with higher sensitivity and specificity. Still, other forms include unique methods, techniques, systems and devices involving a fructosyl peptidyl oxidase.

16 Claims, 11 Drawing Sheets

Phaeosphaeria nodorum fructosyl peptidyl oxidase

MAPSRANTSVIVVGGGGTIGSSTALHLVRSGYTPSNVTVLDAYPIPSSQSAGNDLNKIMG
VSLRNPVDLQLALEARQMWNEDELFKKFFHNTGRLDCAHGEKDIADLKSGYQALVDAGLD
ATNEWLDSEDEILKRMPLLSRDQIKGWKAIFSKDGGWLAAAKAINAVGEYLRDQGVRFGF
YGAGSFKAPLLAEGVCIGVETVDGTRYYADKVVLAAGAWSPTLVELHEQCVSKAWVYGHI
QLTPEEAARYKNSPVVYNGDVGFFFEPNEHGVIKVCDEFPGFTRFKMHQPFGAKAPKRIS
VPRSHAKHPTDTIPDASDVSIRRAIATFMPQFKNKKMFNQAMCWCTDTADAALLICEHPE
WKNFVLATGDSGHSFKLLPNIGKHVVELLEGTLADDLAHAWRWRPGSGDALKSRRSAPAK
DLADMPGWNHDKPRANL (SEQ ID NO:1)

SEQUENCE LISTING

<160> NUMBER OF SEQ ID NOS: 1

<210> SEQ ID NO 1
<211> LENGTH: 437
<212> TYPE: PRT
<213> ORGANISM: Phaeosphaeria nodorum

<400> SEQUENCE: 1

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Ser Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
                100                 105                 110

Ala Leu Val Asp Ala Gly Leu Asp Ala Thr Asn Glu Trp Leu Asp Ser
            115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
                180                 185                 190

Glu Gly Val Cys Ile Gly Val Glu Thr Val Asp Gly Thr Arg Tyr Tyr
            195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
                260                 265                 270

Ile Lys Val Cys Asp Glu Phe Pro Gly Phe Thr Arg Phe Lys Met His
            275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320
```

```
Ile Arg Arg Ala Ile Ala Thr Phe Met Pro Gln Phe Lys Asn Lys Lys
            325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
            370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
            435
```

FRUCTOSYL PEPTIDYL OXIDASE

CROSS-REFERENCE TO RELATED APPLICATIONS

This application is a continuation of International Application No. PCT/EP/2010/004707 filed Aug. 2, 2010, which claims priority to European Patent Application No. 09009968.0 filed Aug. 3, 2009. Each of the referenced applications is incorporated herein by reference in its entirety.

FIELD OF THE INVENTION

The present application relates to a novel fructosyl peptidyl oxidase (FPOX). More particularly, but not exclusively, the present application relates to a fructosyl peptidyl oxidase which may be used in a kit and a sensor for the measurement of glycated proteins, such as glycated albumin, fructosamine, HbA1c, a fructosyl hexapeptide, fructosyl valine and fructosyl valyl histidine.

BACKGROUND

A glycated protein is generated non-enzymatically via a covalent bond between an amino group on a protein and the reducing terminal of a sugar, and is also referred to as an Amadori compound. In blood, glucose is bound to valine at the N-terminal of the β-chain of hemoglobin to generate glycated hemoglobin (glycohemoglobin; HbA1c). The abundance ratio of HbA1c to hemoglobin (Hb) is higher in patients suffering from diabetes mellitus as compared with a normal healthy individual, and the concentration of HbA1c in blood is known to reflect the blood-sugar level during the past several weeks. Thus, concentration of HbA1c in blood is quite important in clinical tests for diagnosis of diabetes mellitus and in blood-sugar control of patients suffering from diabetes mellitus. The HbA1c concentration in blood may be measured using an enzyme having specificity to fructosyl valine.

Fructosyl amino acid oxidase is an FAD-dependent enzyme which catalyzes a reaction where fructosyl amino acid is oxidized to generate 2-keto-D-glucose and the corresponding amino acid. Fructosyl amino acid oxidases have been isolated from various kinds of organisms and it has been suggested that glycated protein such as glycated albumin, HbA1c and fructosamine may be analyzed using such enzymes.

In order to assay HbA1c with a high specificity, the fructosyl amino acid oxidase preferably has a selectivity toward fructosyl valine compared to fructosyl lysine. More preferably, the fructosyl amino acid oxidase may have an oxidase activity toward fructosyl valyl histidine, which corresponds to the N-terminal two amino acid resides of Hb. Hirokawa et al. (Biochem Biophys Res Commun, 311 (1), 2003, 104-111) discloses fructosyl peptidyl oxidases derived from filamentous bacteria of the genus *Achaetomiella* and *Chaetomius*.

One non-limiting object of the present application is to provide a new fructosyl peptidyl oxidase for use in measurement of glycated proteins. Further objects, embodiments, forms, features, advantages, aspects, and benefits shall become apparent from the following description and drawings.

SUMMARY

Figure 1:
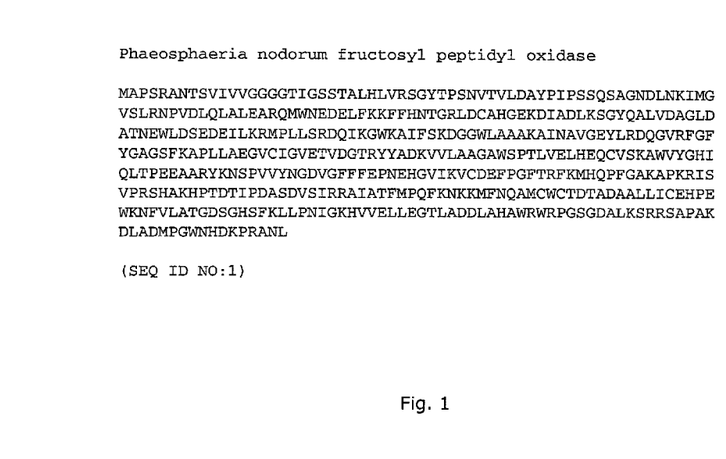
FIG. 1 shows the amino acid sequence of fructosyl peptidyl oxidase from *Phaeosphaeria nodorum*.

The present application is based on a discovery of a fructosyl peptidyl oxidase derived from *Phaeosphaeria nodorum* having the amino acid sequence shown in FIG. 1 (SEQ ID NO:1). In one aspect, a fructosyl peptidyl oxidase for assaying a glycated protein in a sample includes an amino acid sequence having at least 70% identity with the amino acid sequence set forth in SEQ ID NO:1 and a Km value toward fructosyl valyl histidine of 1 mM or less. In another aspect, a fructosyl peptidyl oxidase for assaying a glycated protein in a sample includes an amino acid sequence having at least 70% identity with the amino acid sequence set forth in SEQ ID NO:1 and a Vmax/Km value toward fructosyl valyl histidine of 10 U/mg·mM or more. In yet another aspect, a fructosyl peptidyl oxidase for assaying a glycated protein in a sample includes an amino acid sequence having at least 70% identity with the amino acid sequence set forth in SEQ ID NO:1 and residual activity of 50% or more when heat-treated at 50° C. for 10 minutes.

In another aspect, a method for assaying a glycated protein in a sample includes contacting the sample with a fructosyl peptidyl oxidase described above, and measuring the amount of the glycated protein oxidized by the fructosyl peptidyl oxidase.

In still another aspect, a method for assaying HbA1c includes digesting HbA1c in a sample to generate fructosyl valine or fructosyl valyl histidine, contacting the fructosyl valine or fructosyl valyl histidine with a fructosyl peptidyl oxidase described above, and measuring the amount of oxidized fructosyl valine or fructosyl valyl histidine.

In yet another aspect, a device for assaying fructosyl valine, fructosyl valyl histidine, a fructosyl hexapeptide or HbA1c in a sample includes a fructosyl peptidyl oxidase described above, and an electron transfer mediator. In one form, the electron transfer mediator is N,N-bis-hydroxyethyl-4-nitrosoaniline. In a further form, the device also includes one or more reagents selected from saponin, bilirubin oxidase and proteinase N.

In another aspect, a kit for assaying fructosyl valine, fructosyl valyl histidine, a fructosyl hexapeptide or HbA1c in a sample includes a fructosyl peptidyl oxidase described above and an electron transfer mediator.

In still another aspect, an enzyme electrode includes a fructosyl peptidyl oxidase described above which is immobilized on the electrode. In one form, the fructosyl peptidyl oxidase is immobilized on the electrode using a photo-crosslinkable polyvinyl alcohol resin.

In yet another aspect, an enzyme sensor for assaying fructosyl valine, fructosyl valyl histidine, a fructosyl hexapeptide or HbA1c includes the enzyme electrode described above as a working electrode.

Other aspects include unique methods, techniques, systems and devices involving a fructosyl peptidyl oxidase.

Further embodiments, forms, objects, features, advantages, aspects, and benefits shall become apparent from the following description and drawings.

DETAILED DESCRIPTION

In one embodiment, fructosyl peptidyl oxidase (PnFPOX) is derived from *Phaeosphaeria nodorum* and has the amino acid sequence shown in FIG. 1 (SEQ ID NO:1). In another embodiment, a fructosyl peptidyl oxidase has a modified amino acid sequence with a sequence identity of at least 80% with the amino acid sequence set forth in SEQ ID NO:1. In one aspect, the sequence identity is at least 85%. In another aspect, the sequence identity is at least 90%. In still another aspect, the sequence identity is at least 95%. The genomic sequence of *Phaeosphaeria nodorum* has been published, but this gene has not been annotated. There was no suggestion or implication that *Phaeosphaeria nodorum* has fructosyl peptidyl oxidase or the gene may encode any type of enzyme.

The amino acid sequence of PnFPOX shows 71% identity with FPOX-E (*Eupenicillum terrenum* ATCC 18547; GenBank: BAD00185.1) and 74% identity with FPOX-C (*Coniochaeta* sp. NISL 9330; GenBank: BAD00186.1). The sequence homology with other known fructosyl amino acid oxidases is about 30%.

As described in the Examples below, PnFPOX shows higher activity toward fructosyl valine than toward fructosyl lysine. It also shows even higher activity toward fructosyl valyl histidine. In one form, the Km value toward fructosyl valyl histidine of PnFPOX is 1 mM or less. In another form, the Km value toward fructosyl valyl histidine of PnFPOX is 0.5 mM or less. In still another form, the Km value toward fructosyl valyl histidine of PnFPOX is 0.3 mM or less, which is about ten times lower than that of FPOX-E and FPOX-C. In addition, the Vmax/Km value toward fructosyl valyl histidine of PnFPOX is 10 U/mg·mM or more, which may be desirable for instances in which the enzyme is used for assaying HbA1c with higher sensitivity and specificity.

The fructosyl peptidyl oxidases disclosed herein also exhibit desirable thermostability. For example, when PnFPOX is heat-treated at 50° C. for 10 minutes in 10 mM PPB (pH 7.0), a residual activity of about 75% was observed.

The fructosyl peptidyl oxidases disclosed herein may be prepared by recombinant expression using techniques well known in the art. The nucleic acid sequence of PnFPOX is found in GenBank: XP_001798711.1. The sequence may suitably be modified or designed to achieve greater expression level in a selected host organism. A polynucleotide coding for PnFPOX may be cloned from *Phaeosphaeria nodorum*, or prepared by PCR using a series of chemically synthesized oligonucleotides, or fully synthesized using automated DNA synthesizer.

The gene coding for PnFPOX is inserted into an appropriate expression vector, and the vector is introduced into an appropriate host cell, such as *E. coli*. The transformant is cultured and the fructosyl peptidyl oxidase expressed in the transformant may be collected from the cells or the culture medium.

The recombinant fructosyl peptidyl oxidase thus obtained may be purified by any of the purification techniques known in the art, including but not limited to ion exchange column chromatography, affinity chromatography, liquid chromatography, filtration, ultrafiltration, salt precipitation, solvent precipitation, immunoprecipitation, gel electrophoresis, isoelectric electrophoresis and dialysis.

In one aspect, the fructosyl peptidyl oxidases disclosed herein are useful in assaying a glycated protein in a sample. The assay method comprises contacting the sample with a fructosyl peptidyl oxidase disclosed herein and measuring the amount of the glycated protein oxidized by the fructosyl peptidyl oxidase. Glycated proteins which may be assayed in this manner include, for example, fructosyl valine, fructosyl valyl histidine, a fructosyl hexapeptide, HbA1c, glycated albumin and fructosamine. In one aspect, a method for assaying HbA1c includes digesting HbA1c in a sample to generate fructosyl valine, contacting the fructosyl valine with a fructosyl peptidyl oxidase disclosed herein, and measuring the amount of oxidized fructosyl valine. HbA1c may be digested with a proteinase, such as protease and proteinase N. In one embodiment, the method includes digesting HbA1c in a sample with proteinase N to generate fructosyl valyl histidine, contacting the fructosyl valyl histidine with a fructosyl peptidyl oxidase disclosed herein, and measuring the amount of oxidized fructosyl valyl histidine. In another aspect, a method for assaying HbA1c includes digesting HbA1c by an endoprotease Glu-C to generate a fructosyl hexapeptide, and assaying the fructosyl hexapeptide by a fructosyl peptidyl oxidase disclosed herein. It has now been surprisingly found that fructosyl amino acid oxidase from *Phaeosphaeria nodorum* is capable of oxidizing fructosyl hexapeptide, while FPOX-C of the prior art (*Coniochaeta* sp. NISL 9330; GenBank: BAD00186.1) is not.

Measurement of the amount of the glycated protein oxidized by fructosyl peptidyl oxidase may be effected by measuring the amount of generated $H_2O_2$ by any methods known in the art, for example, using a reagent for $H_2O_2$ detection such as 4AA/TODB/POD (4-aminoantipyrine/N,N-Bis(4-sulfobutyl)-3-methylaniline disodium salt/horseradish peroxidase) or by Pt electrode. Alternatively, the assay may be carried out in the presence of an electron mediator and the amount of electrons transferred to the mediator is measured using, for example, mPMS/DCIP (1-methoxy-5-methylphenazinium methylsulfate/2,6-dichloroindophenol), cPES (trifluoroacetate-1-(3-carboxy-propoxy)-5-ethyl-phenanzinium, NA BM31__1144 (N,N-bis-(hydroxyethyl)-3-methoxy-nitrosoaniline hydrochloride, NA BM31__1008 (N,N-bis-hydroxyethyl-4-nitrosoaniline) and N—N-4-dimethyl-nitrosoaniline. In one particular form, NA_BM31__1008 is utilized.

In another aspect, a device for assaying fructosyl valine, fructosyl valyl histidine, a fructosyl hexapeptide or HbA1c in a sample includes a fructosyl peptidyl oxidase disclosed herein.

The assay device may have a structure similar to conventional, commercially available amperometric biosensor test strips for monitoring blood glucose levels. One example of such a device has two electrodes (a working electrode and a reference or counter electrode) positioned on an insulating substrate, a reagent port and a sample receiver. The reagent port contains a fructosyl peptidyl oxidase disclosed herein, FAD, and an electron transfer mediator. When a sample such as a blood sample is added to the sample receiver, fructosylamine contained in the sample will react with fructosyl peptidyl oxidase to generate current, which is indicative of the amount of fructosylamine in the sample. When whole blood is used as the sample, the device may also include a reagent for hemolysis. One non-limiting hemolysis reagent is saponin. In another embodiment, the device may also include bilirubin oxidase (BOD) in order to reduce the background current of the sensor caused by reducing ingredients contained in the whole blood sample. In another embodiment, the device may also contain proteinase N to effect release of fructosyl valine or fructosyl valyl histidine from glycated albumin present in the blood. Saponin, BOD and proteinase N may be separately immobilized on the device, such that the whole blood sample is contacted with Saponin to affect hemolysis and then contacted with BOD and proteinase N. Non-limiting examples of electrochemical sensors suited for the determination of enzyme substrates are known, for example, from International Patent Publication No. WO 2004/113900 and U.S. Pat. No. 5,997,817. As an alternative to electrochemical sensors, the use of optical detection technologies is also contemplated. Typically, such optical devices are based on color changes that occur in a reagent system comprising the enzyme, an electron transfer mediator and an indicator. The color changes can be quantified using fluorescence, absorption or remission measurements. Typical examples of optical devices suited for the determination of enzyme substrates are known, for example, from U.S. Pat. Nos. 7,008,799, 6,036,919, and 5,334,508.

In yet another aspect, a kit for assaying fructosyl valine, fructosyl valyl histidine, a fructosyl hexapeptide or HbA1c in a sample includes a fructosyl peptidyl oxidase disclosed herein.

A kit for the measurement of fructosyl valine, fructosyl valyl histidine or a fructosyl hexapeptide may be constructed with a fructosyl peptidyl oxidase disclosed herein. In addition to the fructosyl peptidyl, the kit may contain a buffer necessary for measurement, an appropriate mediator, standards of fructosyl valine, fructosyl valyl histidine or a fructosyl hexapeptide or a derivative thereof for the preparation of a calibration curve, and an instruction for use. The kit may also contain an endoprotease Glu-C for digesting HbA1c to generate a fructosyl hexapeptide. The fructosyl peptidyl oxidase may be provided in various forms such as, for example, a freeze-dried reagent or a solution in an appropriate storage solution.

It is also possible to construct a fructosamine, glycated albumin or HbA1c assay kit using a fructosyl peptidyl oxidase disclosed herein. Fructosylamine, glycated albumin or HbA1c is enzymatically or chemically digested to generate a fructosylamine compound such as fructosyl valine or fructosyl valyl histidine, which in turn is quantified using the fructosyl peptidyl oxidase. Accordingly, the assay kit for fructosamine, glycated albumin or HbA1c may further contain a reagent for hydrolysis or a proteinase. One non-limiting proteinase is proteinase N which will digest HbA1c to generate fructosyl valyl histidine.

In another aspect, an enzyme electrode includes a fructosyl peptidyl oxidase disclosed herein immobilized on the electrode. In one form, the fructosyl amino acid oxidase is immobilized on the electrode using a polymer to prevent BOD and proteinase N from contacting with the fructosyl amino acid oxidase and the mediator. Otherwise, BOD could interfere with the redox properties of the mediator, and proteinase N could degrade the fructosyl amino acid oxidase. In one form, the polymer is a photo-crosslinkable polyvinyl alcohol resin such as, for example, an azide-unit pendant water-soluble photopolymer (AWP) supplied by Toyo Gosei Co., Ltd. (Chiba, Japan), just to provide one non-limiting example. To construct the enzyme electrode, a buffer solution containing AWP, the fructosyl amino acid oxidase and a mediator such as NA_BM31_1008 is applied to the surface of the electrode. After drying the solution, UV light is irradiated to effect crosslinking the polymer.

In another aspect, an enzyme sensor for assaying fructosyl valine, fructosyl valyl histidine, a fructosyl hexapeptide or HbA1c includes the enzyme electrode described above as a working electrode.

The concentration of the fructosylamine in a sample may be determined by measuring the amount of electrons generated by the enzyme reaction. The fructosyl peptidyl oxidase is immobilized on the electrode, which may be one of a carbon electrode, a metal electrode, and a platinum electrode. Immobilization of the enzyme may be effected by cross-linking, encapsulation into a macromolecular matrix, coating with a dialysis membrane, an optical cross-linking polymer, an electroconductive polymer, an oxidation-reduction polymer, or other methods well known to the person skilled in the art, and any combination thereof.

When measurement is conducted in an amperometric system, a carbon electrode, gold electrode or platinum electrode with immobilized PnFPOX is used as a working electrode, together with a counter electrode (such as a platinum electrode) and a reference electrode (such as an Ag/AgCl electrode). The electrodes are inserted into a buffer containing a mediator and kept at a predetermined temperature. Predetermined voltage is applied to the working electrode, then a sample is added and increased value in electric current is measured. Examples of the mediator which may be used in the assay include potassium ferricyanide, ferrocene, osmium derivative, ruthenium derivative, phenazine methosulfate, etc. It is generally also possible to use so-called two-electrode systems with one working electrode and one counter or pseudo-reference electrode.

To prepare a sensor for the measurement of fructosylamine, glycated albumin or HbA1c, the above-mentioned sensor for the measurement of fructosyl valine or fructosyl valyl histidine is further combined with a membrane containing immobilized proteinase (such as proteinase N or protease) to construct a complex sensor. In one particular form, proteinase N is used. The structure of such a complex sensor based on a continuous reaction by a combination of plural enzymes is well known in the art. See, for example, "Biosensor—Fundamental and Applications" by Anthony P. F. Tuner, Isao Karube and George S. Wilson, Oxford University Press, 1987.

The contents of all patents and reference documents cited in the present specification are entirely incorporated herein by reference.

EXAMPLES

The following examples are for illustration purposes and are not to be construed as limiting the invention disclosed in this document to only the embodiments disclosed in these examples.

Example 1

Preparation of *Phaeosphaeria nodorum* Fructosyl Peptidyl Oxidase

The nucleotide sequence of the PnFPOX is found in a genomic information of *Phaeosphaeria nodorum* in a public database (GenBank: XP_001798711.1). As the putative ORF contained several minor codons in *E. coli*, the codon usage of the gene was optimized in order to express the gene in *Escherichial coli*. After this optimization, no significant minor codon exists in the sequence. The synthetic gene was subcloned into an expression vector pET28a to construct pEPN (pET28a-PnFPOX).

*E coli* BL21(DE3) cells transformed with PnFAOD expression vector (pEPN) were cultured in 50 ml LB medium supplemented with 50 μg/ml Kanamycin at 37° C., and IPTG (f.c.0.4 mM) were added at OD660 nm=0.8. The cultivation was continued at 25° C. until OD660 nm reached about 3. The cells were collected by centrifugation (5,000×g, 4° C., 10 min), washed (0.85% NaCl aq., 6,000×g, 4° C., 5 min), suspended in 3 ml of 10 mM PPB (pH 7.0), and homogenized by an ultrasonic homogenizer. The resulting suspension was centrifuged (10,000×g, 4° C., 20 min), and the supernatant was further centrifuged (60,000 rpm, 4° C., 60 min). The supernatant was dialyzed against 10 mM PPB (pH7.0) plus 25 μM FAD to obtain a water-soluble fraction. In SDS-PAGE analysis, the water-soluble fraction showed a band at about 48~50 kDa, which is consistent with the predicted molecular weight of PnFPOX.

The water-soluble fraction was examined for the oxidase activity using a POD/TODB/4A.A. method with three substrates: fructosyl valine (FV), fructosyl lysine (FK), and fructosyl valyl histidine (FVH). The fructosyl peptidyl oxidase showed oxidizing activity to fructosyl amino acid (FV, FK) but also to fructosyl dipeptide (FVH).

Example 2

Figure 2:
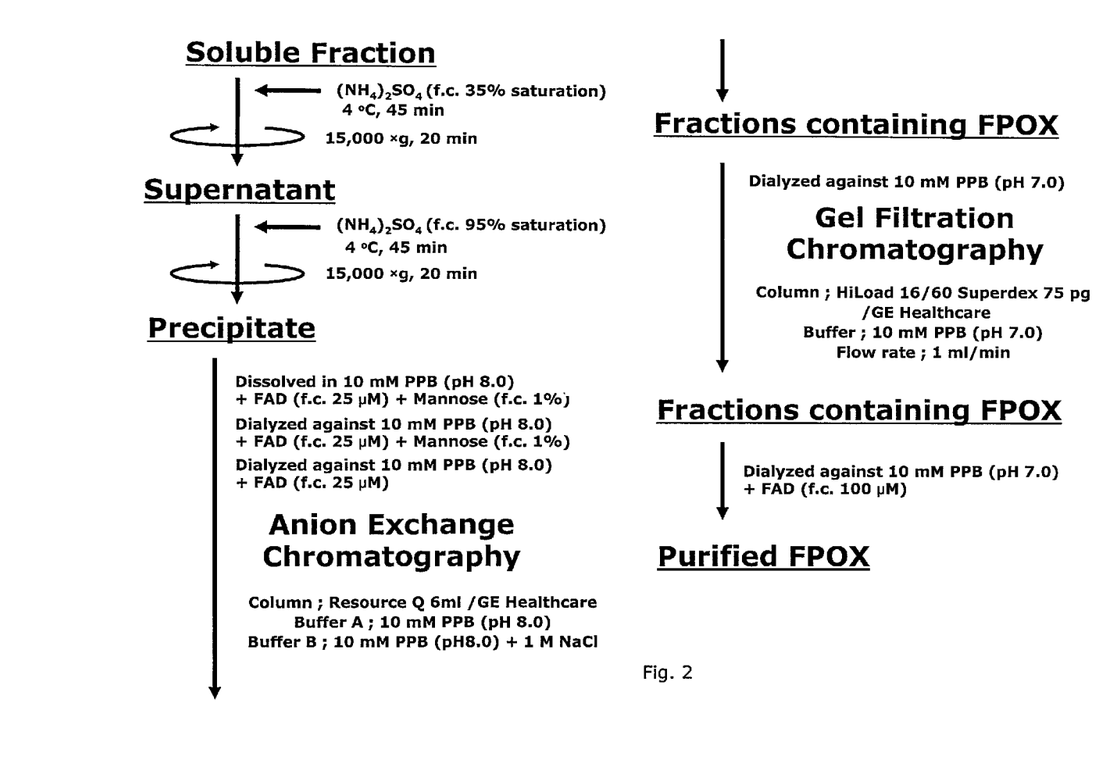
FIG. 2 shows a purification procedure of fructosyl peptidyl oxidase.

Purification and Characterization of *Phaeosphaeria nodorum* Fructosyl Peptidyl Oxidase The purification procedure is summarized in FIG. 2. *Escherichia coli* BL21 (DE3) transformed with pEPN (pET28a-PnFPOX) was grown aerobically at 37° C. in LB medium (7 L) containing 50 μg kanamycin ml$^{-1}$. After reaching an A660 nm value of 1.4, the cells were induced with 0.3 mM IPTG, and the incubation was continued at 25° C. until reaching an A660 nm value of 3.0. The cells were harvested by centrifugation and a quarter of harvested cells (approx. 10.5 g) were resuspended in 10 mM PPB, pH 7.0, and lysed by 2 passages through a French press (1,000 kg cm$^{-2}$). The lysate was centrifuged at 10,000 g at 4° C. for 20 min, and the supernatant was centrifuged at 40,000 rpm at 4° C. for 90 min. The supernatant was then dialyzed against 10 mM PPB, pH 8.0, containing 25 μM FAD.

Ammonium sulfate was added to the dialyzed supernatant to 35% saturation and then the precipitate formed was pelleted by centrifugation at 15,000 g for 20 min. The resultant precipitate was dissolved in 10 mM PPB, pH 8.0, containing 25 μM FAD and 1% mannose and dialyzed at 4° C. against the same buffer, and subsequently dialyzed against 10 mM PPB, pH 8.0, containing 25 μM FAD. The dialyzed enzyme solution was applied to a RESOURCE Q column (GE Healthcare) equilibrated with 10 mM PPB, pH 8.0. The active flow-through fractions were collected, and adsorbed proteins that showed no FAOD activities were eluted with a 1 M NaCl. The active flow-through fractions were collected and dialyzed against 10 mM PPB, pH 7.0.

The dialyzed enzyme solution was applied to a HiLoad 16/60 Superdex 75 pg column (GE Healthcare) equilibrated with 10 mM PPB, pH 7.0. Gel filtration chromatography was carried out with the same buffer. The active fractions were collected, and the purified enzyme solution was dialyzed against 10 mM PPB, pH 7.0 containing 100 μM FAD, and stored at 4° C. The purity of the purified enzyme was confirmed by SDS-PAGE, and the protein concentration was measured using a DC Protein Assay Kit (Bio-Rad, CA, USA).

As summarized in Table 1, PnFPOX was purified 35-fold by ammonium sulfate precipitation, anion exchange chromatography, and gel filtration chromatography from the cell extract of *E. coli* BL21(DE3)/pEPN(pET28a-PnFPOX). The purified preparations showed a nearly single band on SDS-PAGE.

TABLE 1

Purification of recombinant PnFPOX.

| Stage | Total activity (U) | Total Protein (mg) | Specific Activity (U/mg) | Purification (Fold) | Yield (%) |
|---|---|---|---|---|---|
| Soluble fraction | 298 | 526 | 0.57 | 1 | 100 |
| Ammonium Sulfate | 243 | 415 | 0.59 | 1.03 | 82 |
| Resource Q | 189 | 23.9 | 7.9 | 13.9 | 63 |
| HiLoad 1 | 52.9 | 2.69 | 20 | 34.8 | 18 |

Figure 3:
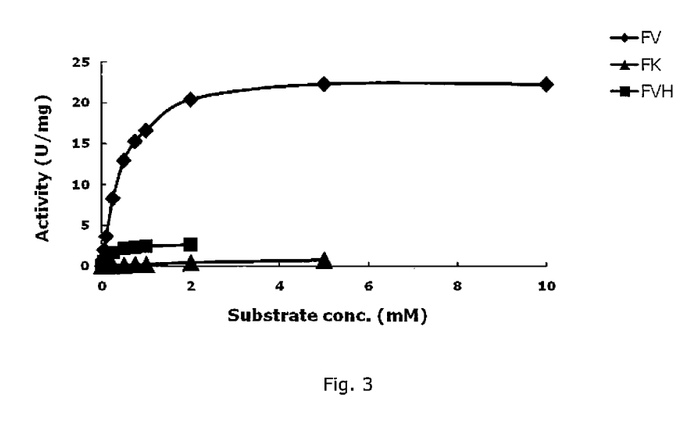
FIG. 3 shows the SV curve of purified fructosyl peptidyl oxidase.

The oxidase activity was assayed using 4A.A/TODB/POD with varying concentrations of substrates, FV, FK and FVH. The absorbance at 546 nm was monitored. The results are shown in FIG. 3. Typical Michaelis-Menten curves were obtained with FV and FVH, but not with FK. Apparent Km values are 0.64 mM for FV and 0.20 mM for FVH (Table 2). A high VmaxKm$^{-1}$ value for FV (42.8 U mg$^{-1}$ mM$^{-1}$) indicates high specificity toward FV of this enzyme. It should be noted that VmaxKm$^{-1}$ value for FVH is also considerable (14.7 U mg$^{-1}$ mM$^{-1}$, 34% of VmaxKm$^{-1}$ for FV). This activity toward FVH of PnFPOX will be beneficial in the enzyme-based measurement of HbA1c. For comparison, the oxidase activity of known fructosyl peptidyl oxidases (FPOX-C and FPOX-E) was also included in the table (Hirokawa et al. ibid).

TABLE 2

Kinetic parameters of fructosyl peptidyl oxidases

| | FV | | | FK | | | FVH | | |
|---|---|---|---|---|---|---|---|---|---|
| | $K_m$ (mM) | $V_{max}$ (U/mg) | $V_{max}/K_m$ | $K_m$ (mM) | $V_{max}$ (U/mg) | $V_{max}/K_m$ | $K_m$ (mM) | $V_{max}$ (U/mg) | $V_{max}/K_m$ |
| PnFPOX | 0.64 | 27.6 | 42.8 | 16 | 3.23 | 0.206 | 0.20 | 2.97 | 14.7 |
| FPOX-C | 0.824 | 66.0 | 80.1 | 10.6 | 23.4 | 2.17 | 2.81 | 23.8 | 8.47 |
| FPOX-E | 0.318 | 20.6 | 64.8 | ND | 0.42 | — | 2.76 | 5.43 | 1.97 |

Figure 4:
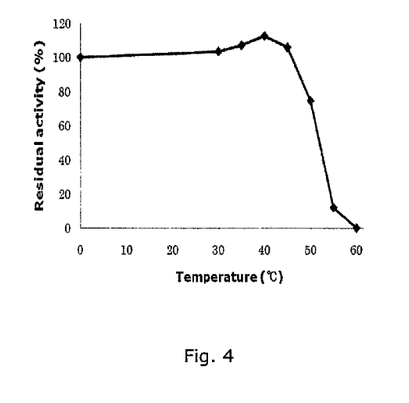
FIG. 4 shows the thermostability of fructosyl peptidyl oxidase.

Thermostability of PnFPOX was evaluated by incubating the purified enzyme solution in 10 mM PPB (pH 7.0) at various temperatures for 10 minutes and then measuring the residual activity. The result is shown in FIG. 4. The activity of PnFPOX was maintained about 75% up to 50° C. This is in contrast with the known fructosyl peptidyl oxidases (FPOX-C and FPOX-E), which lose almost all activity at 50° C. (Hirokawa et al. ibid).

Example 3

Figure 5:
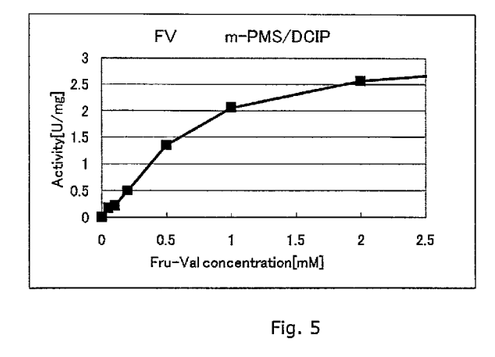
FIG. 5 shows measurement of fructosyl valine using fructosyl peptidyl oxidase in a m-PMS/DCIP system.

Measurement of Fructosylamines Using Fructosyl Peptidyl Oxidase (1) FV-m-PMS/DCIP System Fructosylvaline (FV) was assayed using PnFPOX in the m-PMS/DCIP system in the presence of 0.6 mM PMS and 0.06 mM DCIP. Absorbance at 600 nm was monitored. The result is shown in FIG. 5. The concentration of FV can be measured within the range between 0.05 mM and 1 mM.

(2) F6P-4AA/TODB/POD

Figure 6:
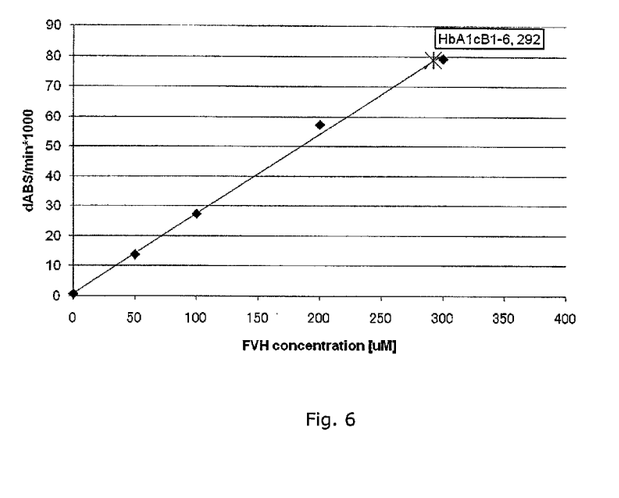
FIG. 6 shows measurement of fructosyl hexapeptide using fructosyl peptidyl oxidase.

A fructosyl hexapeptide (F6P: Fru-Val-His-Leu-Thr-Pro-Glu) having the N-terminus amino acid residues of HbA1c beta-chain was assayed using PnFPOX. To a solution of fructosyl hexapeptide at a final concentration of 300 µM in PBS buffer (pH7.4), Proteinase N derived from Bacillus subtilis (Sigma) was added at a final concentration of 20 mg/ml, and incubated at 37° C. for 10 minutes. Proteinase N was removed with a 10 kDa-cut-off spin column, and the cleaved product was assayed with PnFPOX in a 4AA/TODB/POD system. The amount of the fructosyl hexapeptide in a sample was calculated using the calibration curve prepared with FVH as a substrate. The result showed that 300 µM of FVH was detected (FIG. 6).

(3) HbA1c-4AA/TODB/POD

Figure 7:
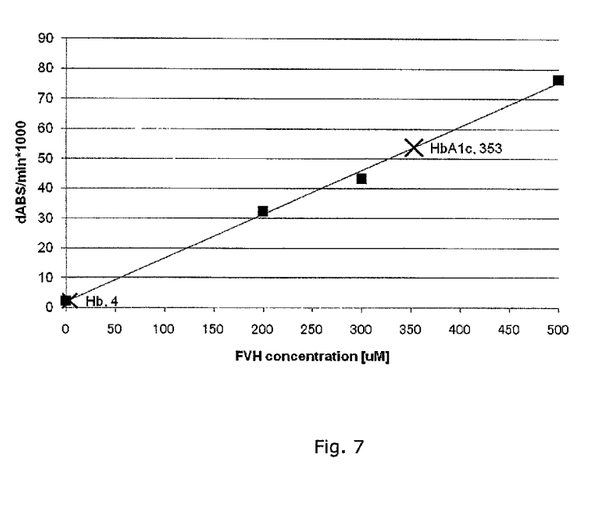
FIG. 7 shows measurement of HbA1c using fructosyl peptidyl oxidase.

Red blood cells were isolated from peripheral blood and purified by a boronic acid column. The absorbed and unabsorbed fractions were designated as HbA1c sample and Hb sample, respectively. These samples were subjected to de-heme treatment in acetone containing 0.2% HCl to prepare De-heme HbA1c and De-heme Hb samples. To a solution of De-heme HbA1c sample and De-heme Hb sample at a final concentration of 300 µM in PBS buffer (pH7.4), Proteinase N was added at a final concentration of 20 mg/ml, and incubated at 37° C. for 10 minutes. Proteinase N was removed with a 10 kDa-cut-off spin column, and the cleaved product was assayed with PnFPOX in a 4AA/TODB/POD system. The amount of the HbA1c in a sample was calculated using the calibration curve prepared with FTV as a substrate in the presence of Proteinase N-treated Hb. The result showed that 350 µM of FVH was detected (FIG. 7). FVH was not detected from Hb, indicating that HbA1c can be specifically detected.

Figure 8:
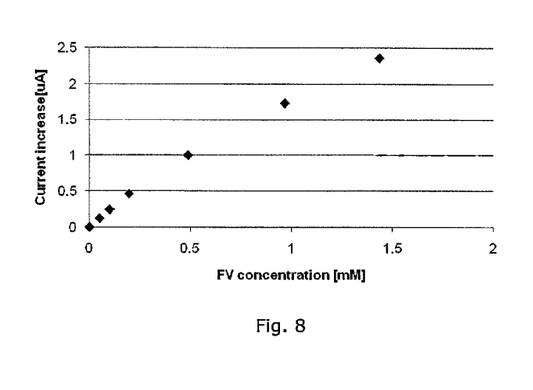
FIG. 8 shows measurement of fructosyl valine using an electrode having fructosyl peptidyl oxidase in a $H_2O_2$ system.

(4) FV-Electrode-$H_2O_2$ System 3.3 ul (0.04 U) of PnFPOX enzyme solution (12 u/ml) was mixed with 1.7 ul of 6% photocrosslinking resin AWP (Toyo Gosei Kogyo) at a final concentration of 2%, and 5 µl of the mixture was applied on a Pt electrode with a surface area of 7 mm$^2$. The electrode was air-dried at 30° C. for 30 min, and irradiated with UV-light for 1 min to prepare a working electrode. The electrode and a counter electrode (Pt wire) and a reference electrode (Ag/AgCl) were immersed in a 2 ml 50 mM PPB (pH 7.0) and +600 mV vs Ag/AgCl was applied. When the steady state current was observed, the sample solution containing indicated amount of FV was added to the reaction mixture, and current increase was monitored. The result is shown in FIG. 8. The concentration of FV can be measured within the range between 0.05 mM and 1.5 mM.

(5) FV-Electrode-Prussian Blue System

Figure 9:
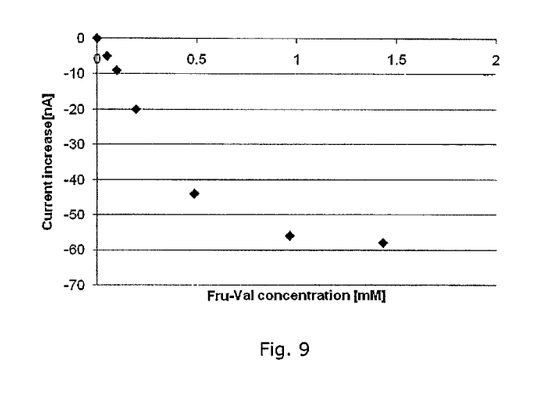
FIG. 9 shows measurement of fructosyl valine using an electrode having fructosyl peptidyl oxidase in a Prussian blue system.

A glassy carbon electrode (BAS, surface area of 7 mm$^2$) was immersed into a solution of 1 mM $FeCl_3$, 1 mM potassiumferricyanide and 2M KCl, and a voltage of +0.4V vs Ag/AgCl was applied for 1 min to prepare a Prussian blue membrane. Then the electrode was subjected to the CV treatment for ten times from −50 mV to +350 mV vs Ag/AgCl with a sweeping rate of 5 mV/sec to stabilize the Prussian blue membrane. The electrode was washed with water and dried. 3.3 ul (0.04 U) of PnFPOX enzyme solution (12 u/ml) was mixed with 1.7 ul of 6% photocrosslinking resin AWP (Toyo Gosei Kogyo) at a final concentration of 2%, and applied on the electrode, and the electrode was air-dried at 30° C. for 30 min, then irradiated with UV-light for 1 min to prepare a Prussian blue-enzyme immobilized electrode as a working electrode. The electrode and a counter electrode (Pt wire) and a reference electrode (Ag/AgCl) were immersed in a 2 ml 50 mM PPB (pH 7.0) and −150 mV vs Ag/AgCl was applied. FV was added to the reaction mixture, and current increase was monitored. The result is shown in FIG. 9. The concentration of FV can be measured within the range between 0.05 mM and 1 mM.

Figure 10:
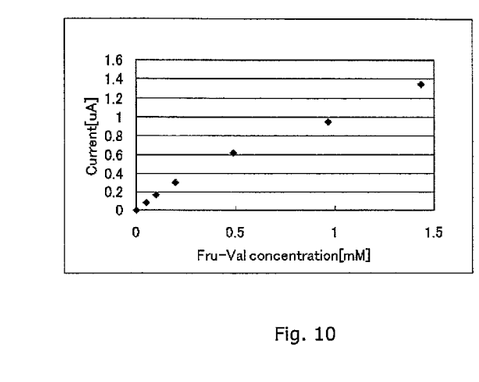
FIG. 10 shows measurement of fructosyl valine using an electrode having fructosyl peptidyl oxidase in a nitrosoaniline (NA) system.

(6) FV-Electrode-NA System 3.3 ul (0.04 U) of PnFPOX enzyme solution (12 u/ml) was mixed with 1.7 ul of 6% photocrosslinking resin AWP (Toyo Gosei Kogyo) at a final concentration of 2%, and 5 µl of the mixture was applied on a gold electrode with a surface area of 7 mm$^2$. The electrode was air-dried at 30° C. for 30 min, and irradiated with UV-light for 1 min to prepare a working electrode. The electrode and a counter electrode (Pt wire) and a reference electrode (Ag/AgCl) were immersed in a 2 ml 50 mM PPB (pH 7.0) containing 5 mM N,N-bis(Hydroxyethyl)-3-methoxy-4-nitrosoaniline (NA) and +200 mV vs Ag/AgCl was applied. FV was added to the reaction mixture, and current increase was monitored. In order to avoid the effect of oxygen, Ar gas was purged into reaction chamber, continuously. The result is shown in FIG. 10. The concentration of FV can be measured within the range between 0.05 mM and 1.5 mM.

(7) FV-Electrode-m-PMS System

Figure 11:
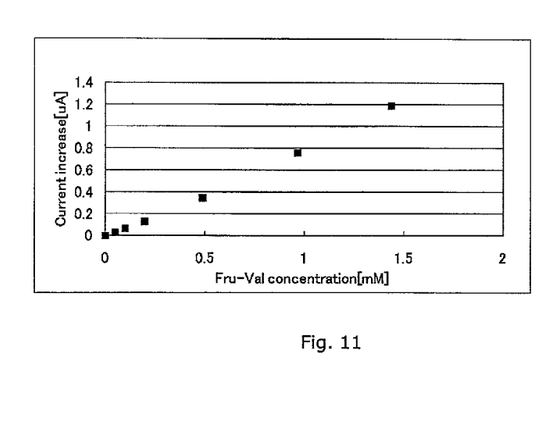
FIG. 11 shows measurement of fructosyl valine using an electrode having fructosyl peptidyl oxidase in a m-PMS system.

PnFPOX-immobilized gold electrode was prepared as described in (4) above. The electrode and a counter electrode (Pt wire) and a reference electrode (Ag/AgCl) were immersed in a 2 ml 50 mM PPB (pH 7.0) containing 2 mM m-PMS and +100 mV vs Ag/AgCl was applied. FV was added to the reaction mixture, and current increase was monitored. The result is shown in FIG. 11. The concentration of FV can be measured within the range between 0.05 mM and 1.5 mM.

Example 4

Oxidase Activity of Fructosyl Peptidyl Oxidase Toward Fructosyl Hexapeptide

The oxidase activity of the fructosyl peptidyl oxidases PnFPOX and FPOX-C on a fructosyl hexapeptide (F6P: Fru-Val-His-Leu-Thr-Pro-Glu) was assayed without addition of Proteinase N. The enzyme activity was measured in a 4AA/TODB/POD system as described in Example 2, with the substrate concentration of 1 mM for FV and FVH and 5 mM for F6P. The result is shown in Table 3.

TABLE 3

|  | FV (U/mg) | FVH (U/mg) | F6P (U/mg) |
| --- | --- | --- | --- |
| PnFPOX | 1.3 | 0.11 | $1.3 \times 10^{-3}$ |
| FPOX-C | 2.3 | 0.60 | n.d |

The fructosyl peptidyl oxidase PnFPOX was capable of oxidizing fructosyl hexapeptide.

In one non-limiting application, the fructosyl peptidyl oxidases disclosed herein may be used for the measurement of glycated proteins, such as hemoglobin (HbA1c) which is clinically useful in diagnosis and control of diabetic conditions. Still, it should be appreciated that alternative applications and uses for the fructosyl peptidyl oxidases disclosed herein are also contemplated.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A device for assaying fructosyl valine, fructosyl valyl histidine, a fructosyl hexapeptide or HbA1c in a sample, comprising an electron transfer mediator and one of:
  a fructosyl peptidyl oxidase comprising an amino acid sequence having at least 90% identity with the amino acid sequence set forth in SEQ ID NO:1 and a Km value toward fructosyl valyl histidine of 1 mM or less;
  a fructosyl peptidyl oxidase comprising an amino acid sequence having at least 90% identity with the amino acid sequence set forth in SEQ ID NO:1 and a Vmax/Km value toward fructosyl valyl histidine of 10 U/mg·mM or more; and
  a fructosyl peptidyl oxidase comprising an amino acid sequence having at least 90% identity with the amino acid sequence set forth in SEQ ID NO:1 and residual activity of 50% or more when heat-treated at 50° C. for 10 minutes.

2. The device of claim 1, wherein the electron transfer mediator is N,N-bis-hydroxyethyl-4-nitrosoaniline.

3. The device of claim 2, further comprising one or more reagents selected from saponin, bilirubin oxidase and proteinase N.

4. The device of claim 1, further comprising one or more reagents selected from saponin, bilirubin oxidase and proteinase N.

5. A kit for assaying fructosyl valine, fructosyl valyl histidine, a fructosyl hexapeptide or HbA1c in a sample, comprising an electron transfer mediator and one of:
  a fructosyl peptidyl oxidase comprising an amino acid sequence having at least 90% identity with the amino acid sequence set forth in SEQ ID NO:1 and a Km value toward fructosyl valyl histidine of 1 mM or less;
  a fructosyl peptidyl oxidase comprising an amino acid sequence having at least 90% identity with the amino acid sequence set forth in SEQ ID NO:1 and a Vmax/Km value toward fructosyl valyl histidine of 10 U/mg·mM or more; and
  a fructosyl peptidyl oxidase comprising an amino acid sequence having at least 90% identity with the amino acid sequence set forth in SEQ ID NO:1 and residual activity of 50% or more when heat-treated at 50° C. for 10 minutes.

6. The kit of claim 5, wherein the electron transfer mediator is N,N-bis-hydroxyethyl-4-nitrosoaniline.

7. The kit of claim 6, further comprising one or more reagents selected from saponin, bilirubin oxidase and proteinase N.

8. The kit of claim 5, further comprising one or more reagents selected from saponin, bilirubin oxidase and proteinase N.

9. An enzyme electrode, comprising one of:
  a fructosyl peptidyl oxidase comprising an amino acid sequence having at least 90% identity with the amino acid sequence set forth in SEQ ID NO:1 and a Km value toward fructosyl valyl histidine of 1 mM or less;
  a fructosyl peptidyl oxidase comprising an amino acid sequence having at least 90% identity with the amino acid sequence set forth in SEQ ID NO:1 and a Vmax/Km value toward fructosyl valyl histidine of 10 U/mg·mM or more; and
  a fructosyl peptidyl oxidase comprising an amino acid sequence having at least 90% identity with the amino acid sequence set forth in SEQ ID NO:1 and residual activity of 50% or more when heat-treated at 50° C. for 10 minutes; and
  wherein the fructosyl peptidyl oxidase is immobilized on the electrode.

10. The enzyme electrode of claim 9, wherein the fructosyl peptidyl oxidase is immobilized on the electrode using an azide-unit pendant water-soluble photopolymer (AWP).

11. The enzyme electrode of claim 10, further comprising N,N-bis-hydroxyethyl-4-nitrosoaniline immobilized on the electrode.

12. The enzyme electrode of claim 9, further comprising N,N-bis-hydroxyethyl-4-nitrosoaniline immobilized on the electrode.

13. An enzyme sensor for assaying fructosyl valine, fructosyl valyl histidine, a fructosyl hexapeptide or HbA1c, comprising a working electrode including one of:
  a fructosyl peptidyl oxidase comprising an amino acid sequence having at least 90% identity with the amino acid sequence set forth in SEQ ID NO:1 and a Km value toward fructosyl valyl histidine of 1 mM or less;
  a fructosyl peptidyl oxidase comprising an amino acid sequence having at least 90% identity with the amino acid sequence set forth in SEQ ID NO:1 and a Vmax/Km value toward fructosyl valyl histidine of 10 U/mg·mM or more; and a fructosyl peptidyl oxidase comprising an amino acid sequence having at least 90% identity with the amino acid sequence set forth in SEQ ID NO:1 and residual activity of 50% or more when heat-treated at 50° C. for 10 minutes; and wherein the fructosyl peptidyl oxidase is immobilized on the electrode.

14. The enzyme electrode of claim 13, wherein the fructosyl peptidyl oxidase is immobilized on the electrode using an azide-unit pendant water-soluble photopolymer (AWP).

15. The enzyme electrode of claim 14, further comprising N,N-bis-hydroxyethyl-4-nitrosoaniline immobilized on the electrode.

16. The enzyme electrode of claim 13, further comprising N,N-bis-hydroxyethyl-4-nitrosoaniline immobilized on the electrode.

* * * * *